(12) United States Patent
Baillet et al.

(10) Patent No.: US 12,721,960 B2
(45) Date of Patent: Sep. 1, 2026

(54) DEVICE FOR NASAL DELIVERY OF A FLUID PRODUCT

(71) Applicant: APTAR FRANCE SAS, Le Neubourg (FR)

(72) Inventors: Matthieu Baillet, Rouen (FR); Guillaume Du Boisbaudry, Bois Guillaume (FR)

(73) Assignee: APTAR FRANCE SAS, Le Neubourg (FR)

( * ) Notice: Subject to any disclaimer, the term of this patent is extended or adjusted under 35 U.S.C. 154(b) by 427 days.

(21) Appl. No.: 18/572,363

(22) PCT Filed: Jul. 4, 2022

(86) PCT No.: PCT/FR2022/051324
§ 371 (c)(1),
(2) Date: Dec. 20, 2023

(87) PCT Pub. No.: WO2023/281194
PCT Pub. Date: Jan. 12, 2023

(65) Prior Publication Data

US 2024/0277954 A1 Aug. 22, 2024

(30) Foreign Application Priority Data

Jul. 5, 2021 (FR) ...................................... 2107264

(51) Int. Cl.
*A61M 15/08* (2006.01)
*A61M 11/02* (2006.01)
*A61M 15/00* (2006.01)

(52) U.S. Cl.
CPC ........... *A61M 15/08* (2013.01); *A61M 11/02* (2013.01); *A61M 15/009* (2013.01)

(58) Field of Classification Search
CPC ...... A61M 11/00; A61M 11/02; A61M 11/06; A61M 11/08; A61M 15/00–0001;
(Continued)

(56) References Cited

U.S. PATENT DOCUMENTS

2002/0008164 A1* 1/2002 Yanagida ............ B05B 12/0026 239/525
2015/0053207 A1* 2/2015 Knell .................. A61M 15/009 128/203.12

(Continued)

FOREIGN PATENT DOCUMENTS

EP 0 969 891 B1 6/2003
WO 99/46055 A1 9/1999

(Continued)

OTHER PUBLICATIONS

International Preliminary Report on Patentability (with translation of Written Opinion) dated Dec. 14, 2023 issued in International Application No. PCT/FR2022/051324.

(Continued)

*Primary Examiner* — Rachel T Sippel
(74) *Attorney, Agent, or Firm* — Sughrue Mion, PLLC

(57) ABSTRACT

Device having a vessel containing a fluid product dose, a compressed gas vessel for dispensing a dose of compressed gas to expel the dose of fluid product, and an intermediate portion having a body and a connection for connecting the vessel to the compressed gas vessel, and an actuating mechanism. The connection has first and second support members and a deformable tube attached thereto. The first support member has a first opening mechanism for opening the vessel and the second support member has a second opening mechanism for opening the compressed gas vessel. A spring is between the first and second support members, the actuating mechanism has a button rigidly connected to a cage which locks the support members axially. When the (Continued)

Figures 1, 2, 3, 4:
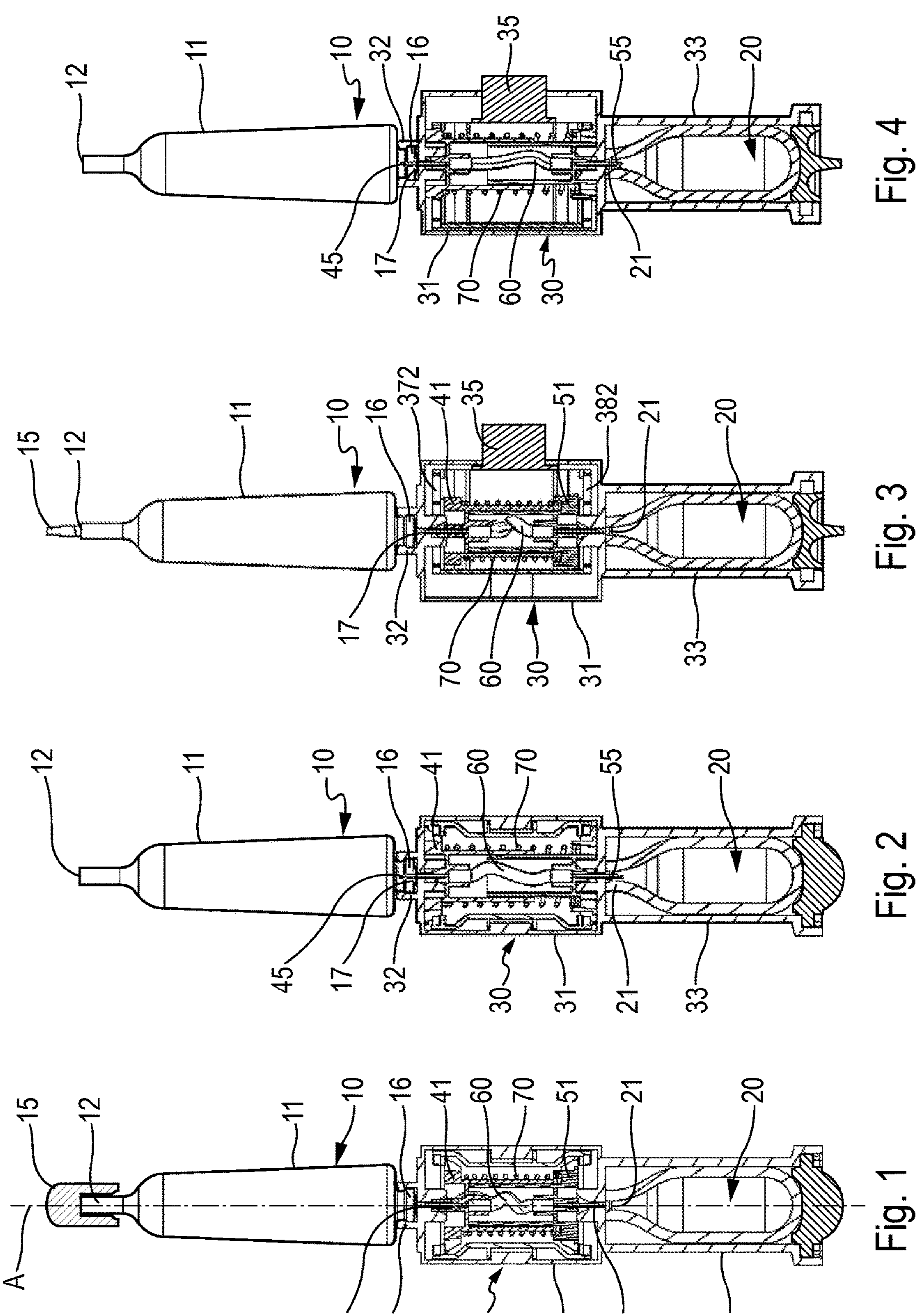

button is moved radially, the support members are unlocked and the spring moves the two support members towards their actuating positions.

15 Claims, 3 Drawing Sheets

(58) Field of Classification Search
CPC .... A61M 15/002; A61M 15/0028–003; A61M 15/0033–0036; A61M 15/009; A61M 15/06–08; B65D 47/36; B65D 51/002; B65D 51/2814–2835; B65D 2517/00; B65D 83/162; B05B 12/002
See application file for complete search history.

(56) References Cited

U.S. PATENT DOCUMENTS

| | | | |
|---|---|---|---|
| 2018/0193575 A1* | 7/2018 | Hieronymus | ..... A61M 15/0028 |
| 2020/0121871 A1 | 4/2020 | Genosar | |
| 2020/0197633 A1 | 6/2020 | Shahaf et al. | |
| 2020/0261666 A1* | 8/2020 | Eicher | ................. B05B 11/1081 |

FOREIGN PATENT DOCUMENTS

| | | |
|---|---|---|
| WO | 02/45866 A1 | 6/2002 |
| WO | 2020/154182 A1 | 7/2020 |

OTHER PUBLICATIONS

International Search Report for PCT/FR2022/051324 dated Oct. 31, 2022.

* cited by examiner

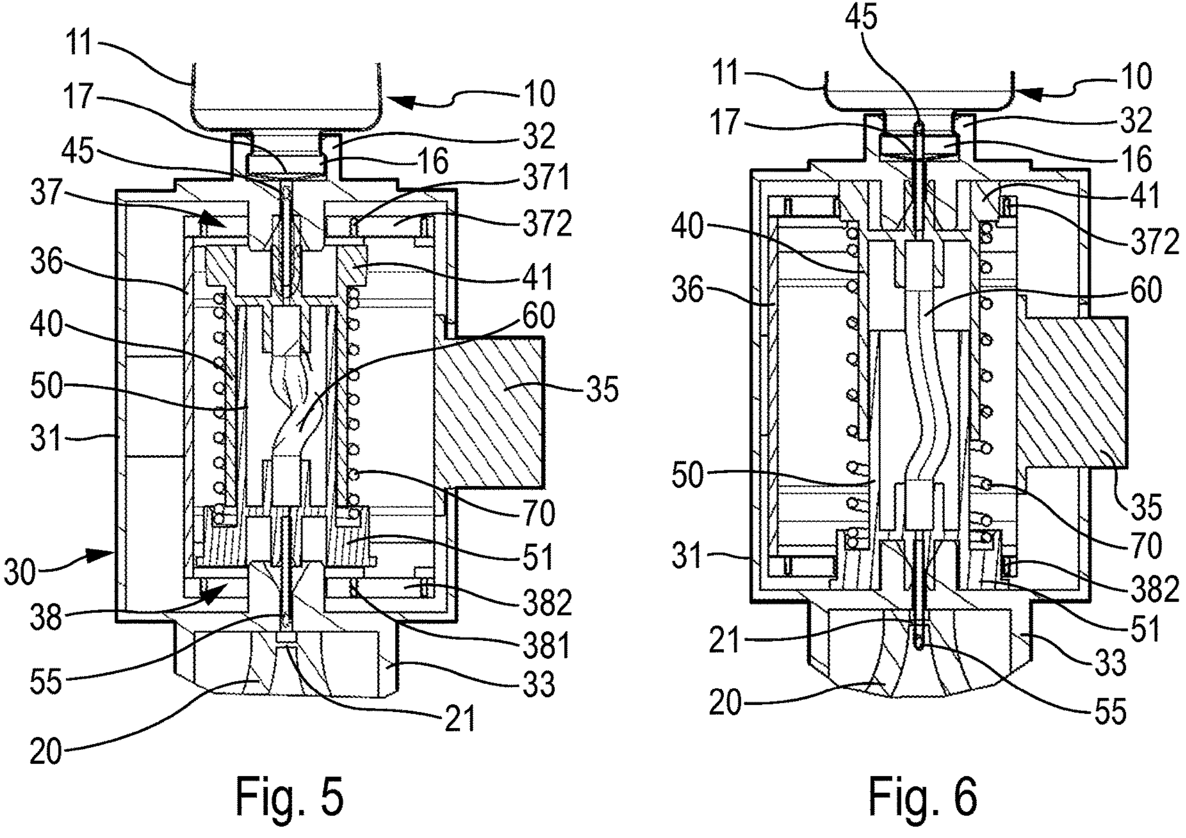
Fig. 5
Fig. 6
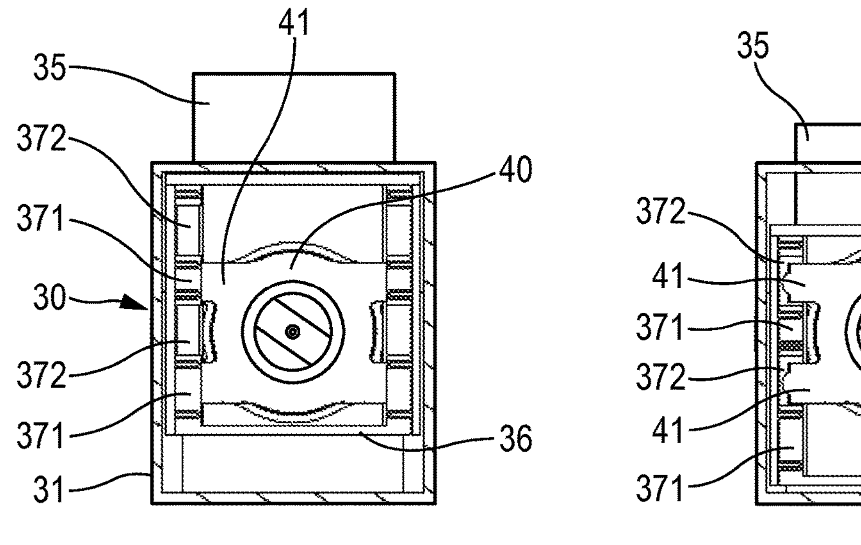
Fig. 7
Fig. 8

15
12
11
10
32
31
35
30
33
20

12
11
10
17
16
32
45
31
36
70
60
35
26
30
25
20
33

DEVICE FOR NASAL DELIVERY OF A FLUID PRODUCT

CROSS REFERENCE TO RELATED APPLICATIONS

This application is a National Stage of International Application No. PCT/FR2022/051324 filed Jul. 4, 2022, claiming priority based on French Patent Application No. FR2107264 filed Jul. 5, 2021.

The present invention relates to a device for nasal delivery of fluid product, and more specifically, a device for dispensing into a nostril, a dose of pharmaceutical fluid product, in particular liquid or powder, contained in a vessel, using a pressurised gas flow.

Documents WO9946055 and WO0245866 disclose nasal delivery devices, wherein a spherical closing element, which blocks the outlet of the vessel, is expelled by the airflow created by an air purge actuated manually by the user. A disadvantage of this type of device is the manual air expeller, which can in the example of document WO9946055 deliver a variable air flow depending on the way in which the device is actuated. A disadvantage of this type of device is the manual air purge, which can, in the example of document WO9946055, deliver a variable airflow according to the way in which the device is actuated. Document WO0245866 resolves this problem by proposing an actuating end position mechanical opening, but to guarantee a sufficient airflow, the actuation of the air purge can prove to be difficult for vulnerable people.

Document WO2020154182 proposes to replace the manual air purge by a compressed gas vessel which is opened during actuation to dispense the dose of fluid product. The device comprises a double-pointed needle, and when the user presses on the bottom of the vessel, the needle will pierce both the fluid product vessel and the compressed gas vessel, thus enabling the compressed gas to dispense the dose of fluid product. This implementation has the disadvantage of having to exert an axial force, while the device is in the nostril of the user, with risks of discomfort or injury during the triggering of the compressed gas flow.

Document US2020121871 describes another prior-art device.

An object of the present invention is to provide a device for nasal delivery of fluid product that does not have the above-mentioned drawbacks.

The present invention, in particular, aims to provide such a device which guarantees the expulsion of the dose of fluid product, independently from the speed or from the actuating force.

The present invention also aims to provide such a device which prevents any risk of injury in the nostril during actuation.

The present invention also aims to provide such a device which is simple and inexpensive to manufacture, to assemble, to fill and to use.

The present invention therefore aims for a fluid product dispensing device, comprising a vessel containing a dose of fluid product to be dispensed, a compressed gas vessel suitable for dispensing a dose of compressed gas to expel the dose of fluid product during actuation, and an intermediate portion comprising a body and connection means for connecting said fluid product vessel to said compressed gas vessel, and actuating means for actuating said device, said connection means comprising a first support member and a second support member movable axially with respect to said body, and a flexible and deformable tube attached both to said first support member and to said second support member, said first support member comprising first opening means for, in the actuating position, opening said fluid product vessel, and said second support member comprising second opening means for, in the actuating position, opening said compressed gas vessel, a loaded spring being disposed between said first and second support members, for elastically urging them to their respective actuating position, said actuating means comprising an actuating button which can move radially between a rest position and an actuating position, said actuating button being rigidly connected to a hollow cage which, in the rest position of said actuating button, locks said support members axially in their respective rest positions, and when said actuating button is moved radially to its actuating position, said support members are unlocked axially and said spring moves said two support members to their respective actuating positions.

According to a first advantageous variant, said fluid product vessel contains a single dose of fluid product.

Advantageously, said first opening means comprise a first needle, connected to said flexible tube, and which, in the actuating position, pierces a membrane of said fluid product vessel.

According to a first advantageous variant, said compressed gas vessel contains a single dose of compressed gas.

Advantageously, said second opening means comprise a second needle, connected to said flexible tube, and which, in the actuating position, pierces a membrane of said compressed gas vessel.

According to a second advantageous variant, said compressed gas vessel contains several doses of compressed gas.

Advantageously, said second opening means comprise a valve well, connected to said flexible tube, and which engages with a valve of a dosing valve mounted on said compressed gas vessel.

Advantageously, said hollow cage comprises an upper axial wall and a lower axial wall, each axial wall comprising wall parts and axial openings.

Advantageously, in the rest position, an upper axial edge of said first support member is locked axially by a wall portion of said upper axial wall, and a lower axial edge of said second support member is locked axially by a wall portion of said lower axial wall.

Advantageously, when said actuating button is moved radially to its actuating position, an axial opening of said upper axial wall is positioned facing said upper axial edge of said first support member, and an axial opening of said lower axial wall is positioned facing said lower axial edge of said second support member.

Advantageously, in the rest position, said flexible tube is deformed and/or twisted, and when said two support members move axially relative to one another to their respective actuating positions, said flexible tube straightens, to compensate for the axial gap generated between the two support members during actuation.

Advantageously, during actuation, said fluid product vessel and said compressed gas vessel are opened simultaneously.

In a variant, during actuation, said fluid product vessel is opened just before said compressed gas vessel.

Advantageously, said vessel is of the BFS (Blow-Fill-Seal) or FFS (Form-Fill-Seal) type, i.e. produced by blowing or forming, filling and sealing continuously.

Advantageously, said vessel comprises attachment means for attaching said vessel to said intermediate portion, in particular, removably.

Figures 9, 10:
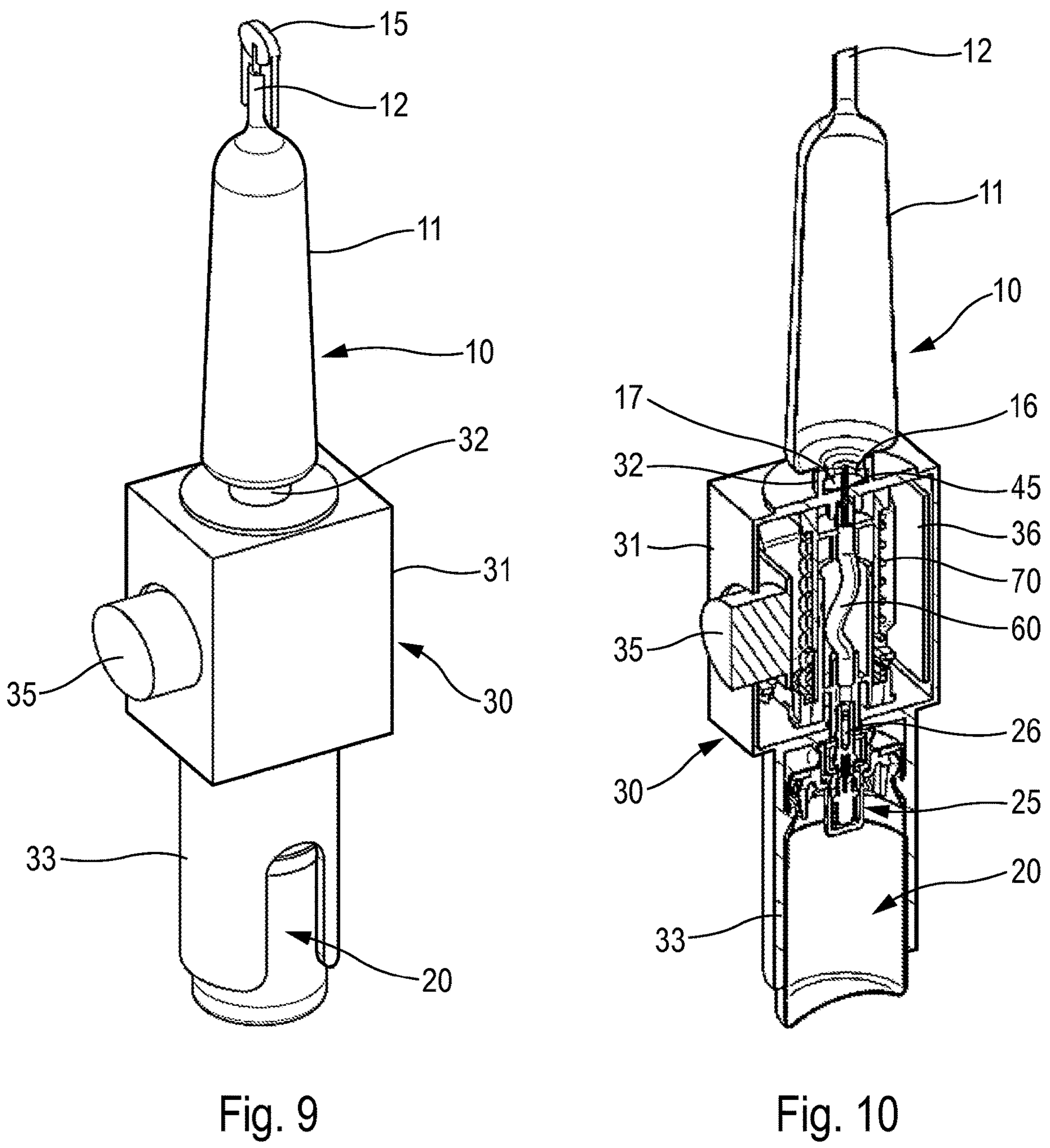

These features and advantages and others will appear more clearly during the detailed description below, made in reference to the accompanying drawings, given as non-limiting examples, and wherein:

FIG. 1 is a schematic, vertical cross-sectional view of a device for dispensing fluid product according to a first advantageous embodiment, before actuation, FIG. 2 is a view similar to that of FIG. 1, shown after actuation, FIGS. 3 and 4 are views similar to those of FIGS. 1 and 2, seen according to a different angle, FIG. 5 is a detailed schematic, vertical cross-sectional view of the device of FIG. 3, FIG. 6 is a detailed schematic, vertical cross-sectional view of the device of FIG. 4, FIG. 7 is a schematic, top, horizontal cross-sectional view of the intermediate portion, before actuation, FIG. 8 is a view similar to that of FIG. 7, shown after actuation, FIG. 9 is a schematic, perspective view of a device for dispensing fluid product according to a second advantageous embodiment, before actuation, and FIG. 10 is a schematic, perspective, cutout view of the device of FIG. 9, after actuation.

It is understood that in the description below, the terms "upper", "lower", "top", "bottom", "vertical" and "horizontal" refer to the upright position of the device represented in FIGS. 1 to 4, 9 and 10. The terms "axial" and "radial" refer to the longitudinal central axis A of the device, represented in FIG. 1.

The device comprises three main portions, namely a vessel 10 containing a dose of fluid product to be dispensed, in particular a medication in powder- or liquid-form, a compressed gas vessel 20 suitable for dispensing a dose of compressed gas during actuation to expel the dose of fluid product during actuation, and an intermediate 30 portion 30 connecting the vessel 10 to the compressed gas vessel 20 and enabling the actuation of the device.

The vessel 10 can be formed directly in an axially elongated dispensing head 11, the axial end of which comprises a dispensing orifice 12, and which is intended to be inserted into the nostril of a user, as represented in the examples of the figures. In a variant, the vessel could be separated from the dispensing head.

In a preferred embodiment, which can be seen in the figures, the vessel 10 is of the BfS (Blow-Fill-Seal) or FFS (Form-Fill-Seal) type, i.e. that the vessel 10 is produced by blowing or forming, filling and sealing continuously, preferably in a sterile enclosure.

The dispensing orifice 12 is closed by a removable stopper 15 which is removed just before the use of the device. After removal of the stopper 15, the dispensing orifice 12 is open.

On the side axially opposite the dispensing orifice 12, the vessel 10 is closed by a membrane 17 suitable for being opened, in particular pierced, during actuation, as will be described below.

Advantageously, the reservoir 10 comprises fastening means 16 for fastening the reservoir 10 to the intermediate portion 30. This attachment can be non-detachable, when the device is single-use and disposable after actuation. In a variant, the attachment can be dismountable, to replace an empty vessel with a full vessel, when the device is reusable. An example of a dismountable attachment would be a rotary attachment of the Luer type, well-known in the field of syringes.

In the first embodiment of FIGS. 1 to 6, the compressed gas vessel 20 contains one single dose of compressed gas. In this case, the compressed gas vessel 20 can be non-detachable from the intermediate portion 30 if the device is single-use and disposable after use. In a variant, the compressed gas vessel 20 could be dismountable to replace an empty gas vessel 20 with a full gas vessel 20, when the device is reusable.

In this first embodiment, the compressed gas vessel 20 is closed by a membrane 21 suitable for being opened, in particular pierced, during actuation, as will be described below.

In the second embodiment of FIGS. 9 and 10, the compressed gas vessel 20 contains several doses of compressed gas.

In this case, the compressed gas vessel 20 preferably comprises a dosing valve 25 comprising a valve 26 which is movable axially in the valve during actuation for dispensing a dose of compressed gas. The opening of the compressed gas vessel 20 thus occurs when the valve 26 is moved to its actuated position, by being pressed axially in the valve body, in a well-known manner. The dosing valves operating with compressed gases are well-known, and the dosing valve 25, which can be of any existing type, will not be described in more detail in this case.

The intermediate portion 30 comprises a body 31 provided with an upper body portion 32 and a lower body portion 33. The upper body portion 32 advantageously comprises complementary attachment means of the attachment means 16 of the vessel 10, for example a standard attachment of the Luer type. The lower body portion 33 receives the compressed gas vessel 20.

An actuating button 35 is mounted radially sliding in the body 31 between a rest position and an actuating position, wherein the actuating button 35 is pressed radially to the inside of the body 31. The actuating button 35 is rigidly connected to a hollow cage 36.

Advantageously, the hollow cage 36 comprises an upper axial wall 37 and a lower axial wall 38, each axial wall 37, 38 comprising wall portions 371, 381 and axial openings 372, 382 which can be seen in FIGS. 5 to 8.

The body 31 of the intermediate portion 30 contains a first support member 40 and a second support member 50 disposed around one another by each being movable axially with respect to the body 31. The first support member 40 is movable axially upward between its rest position and its actuating position, and the second support member 50 is movable axially downward between its rest position and its actuating position.

The first support member 40 comprises an upper axial edge 41 and the second support member 50 comprises a lower axial edge 51.

A flexible and deformable tube 60 is attached both to the first support member 40 and to the second support member 50. In the rest position, this flexible tube is deformed and/or twisted, and when the two support members 40, 50 move axially relative to one another to their respective actuating positions, the flexible tube 60 straightens, thus making it possible to compensate for the axial gap generated between the two support members 40, 50 during actuation.

The first support member 40 comprises first opening means 45 of the fluid product vessel 10. In the examples represented, these first opening means comprise a first needle 45, connected to said flexible tube 60, and which, in the actuating position, pierces the membrane 17 of the vessel 10.

The second support member 50 comprises second opening means 55 of the compressed gas vessel 20. In the example represented in FIGS. 1 to 6, these second opening means comprise a second needle 55, connected to said flexible tube 60, and which, in the actuating position, pierces the membrane 21 of the compressed gas vessel 20.

Thus, in the actuating position, the content of the compressed gas vessel 20 is connected to the content of the fluid product vessel 10 via the two needles 55, 45 and the flexible tube 60, ensuring the dispensing of said fluid product through the dispensing orifice 12.

A loaded spring 70 is disposed between said first and second support members 40, 50, for elastically urging them to their respective actuating position.

The hollow cage 36, in the rest position of the actuating button 35, locks said support members 40, 50 in their rest positions, and when the actuating button 35 is radially moved to its actuating position, the support members 40, 50 are unlocked and the spring 70 moves the two support members 40, 50 to their respective actuating positions. Thus, the actuation of the side actuating button 35 simultaneously generates the opening of the fluid product vessel and the opening of the compressed gas vessel 20. Optionally, in particular by adapting the respective positions of the two support members 40, 50, it is possible to make sure that during actuation, the fluid product vessel 10 is opened just before the opening of the compressed gas vessel 20.

The properties of the spring 70, in particular its stiffness and/or the force that it exerts during actuation on the two support members 40, 50, make it possible to predetermine the performances of the spray generated at the outlet of the dispensing orifice 12.

Other parameters also impact on these performances of the spray, in particular the volume and the pressure of the dose of compressed gas delivered during actuation, as well as the volume of the fluid product contained in the vessel 10.

Advantageously, as represented in FIG. 7, in the rest position, the upper axial edge 41 of the first support member 40 abuts against a wall portion 371 of the upper axial wall 37 of the cage 36 and the lower axial edge 51 of the second support member 50 abuts against a wall portion 381 of the lower axial wall 38 of the cage 36.

When the actuating button 35 is moved radially to its actuating position, represented in FIG. 8, an axial opening 372 of the upper axial wall 37 of the cage 36 is positioned facing said upper axial edge 41 of the first support member 40, and an axial opening 382 of the lower axial wall 38 of the cage 36 is positioned facing said lower axial edge 51 of the second support member 50. The two support members 40, 50 are thus no longer locked axially, and the spring 70 moves each support member 40, 50 to its respective actuating position.

When the user wishes to use the device, they first remove the stopper 15 from the dispensing orifice 12 of the vessel 10, and places the dispensing head in a nostril. They thus press the actuating button 35, this actuating movement being lateral and non-axial, to move the cage 36 radially in the body 31 and release axially the two support members 40, 50. The spring 70 thus automatically actuates and dispenses the dose of fluid product contained in the vessel 10 by means of the compressed gas contained in the compressed gas vessel 20.

After use, the device is disposed of, if it is single-use.

In a variant, it can be considered to reuse the intermediate portion 30, by replacing the empty fluid product vessel 10 with a new fluid product vessel 10 and by replacing the empty compressed gas vessel 20 with a new compressed gas vessel 20. In this case, the actuating button 35 advantageously comprises re-arm means to return it into the rest position after each actuation. Advantageously, these re-arm means comprise an elastic element, such as a second spring. Preferably, the force exerted by this second spring is greater than the force exerted by the spring 70, such that re-arming is done automatically, first by returning the actuating button 35 to its rest position, and also by returning the two support members 40, 50 to their respective rest positions, by refilling the spring 70.

In the second embodiment of FIGS. 9 and 10, a compressed gas vessel 20 is used, containing several doses of compressed gas, the device thus being reusable, with change of the vessel 10 after each actuation.

In this second embodiment, the second support member 50 does not comprise a needle for piercing a membrane, but engages with the valve 26 of the dosing valve 25 mounted on the compressed gas vessel 20. Thus, upon each actuation, a dose of compressed gas is delivered to dispense the fluid product contained in the vessel 10.

With the device being reusable, the actuating button 35 comprises re-arm means to return it into the rest position after each actuation. Advantageously, these re-arm means comprise an elastic element, such as a second spring. Preferably, the force exerted by this second spring is greater than the force exerted by the spring 70, such that re-arming is done automatically, first by returning the actuating button 35 to its rest position, and also by returning the two support members 40, 50 to their respective rest positions, by refilling the spring 70.

The device according to the invention improves the dispensing of the fluid product into the nostril, by enabling the product to reach portions farthest away, such as the ethmoids.

The device according to the invention is, in particular, suitable for being used in the treatment of allergic rhinitis and central pain syndrome.

In the scope of allergic rhinitis, the fluid product can be chosen from the list below, given as a non-limiting example: fluticasone, mometasone, fluticasone furoate, budesonide, beclometasone, azelastine fluticasone, azelastine, tixocortol, triamcinolone acetonide, ipratropium bromide, prednisolone, ciclesonide, flunisolide, levocabastine, azelastine fluticasone furoate, olopatadine, azelastine mometasone, mometasone olopatadine, fluticasone olopatadine.

In the scope of a central pain syndrome, the fluid product can be chosen from the list below, given as a non-limiting example: sumatriptan, zolmitriptan, naloxone, fentanyl, esketamine, midazolam, butorphanol, dihydroergotamine, diazepam, tapentadol, alfentanil, diamorphine, ketorolac.

The present invention has been described in reference to various embodiments and variants, but it is understood that a person skilled in the art, can provide any modifications to it, without moving away from the scope of the present invention such as defined by the accompanying claims.

The invention claimed is:

1. A device for dispensing fluid product, comprising a vessel containing a dose of fluid product to be dispensed, a compressed gas vessel suitable for dispensing a dose of compressed gas to expel the dose of fluid product during actuation, and an intermediate portion comprising a body and connection means for connecting said fluid product vessel to said compressed gas vessel, and actuating means for actuating said device, wherein said connection means comprise a first support member and a second support member movable axially with respect to said body, and a flexible and deformable tube attached both to said first support member and to said second support member, said first support member comprising first opening means, for, in an actuating position, opening said fluid product vessel, and said second support member comprising second opening means for, in an actuating position, opening said compressed gas vessel, a loaded spring being disposed between said first and second support members, for elastically urging the first and second support members to their respective actuating position, said actuating means comprising an actuating button movable radially between a rest position and an actuating position, said actuating button being rigidly connected to a hollow cage which, in the rest position of said actuating button, locks said first and second support members axially in respective rest positions, and when said actuating button is moved radially to its actuating position, said first and second support members are unlocked axially and said spring moves said first and second support members to their respective actuating positions.

2. The device according to claim 1, wherein said fluid product vessel contains a single dose of the fluid product.

3. The device according to claim 1, wherein said first opening means comprise a first needle, connected to said flexible tube, and which, in the actuating position of said first support member, pierces a membrane of said fluid product vessel.

4. The device according to claim 1, wherein said compressed gas vessel contains a single dose of the compressed gas.

5. The device according to claim 4, wherein said second opening means comprise a second needle, connected to said flexible tube, and which, in the actuating position of said second support member, pierces a membrane of said compressed gas vessel.

6. The device according to claim 1, wherein said compressed gas vessel contains several doses of the compressed gas.

7. The device according to claim 6, wherein said second opening means comprise a valve well, connected to said flexible tube, and the valve well engages with a valve of a dosing valve mounted on said compressed gas vessel.

8. The device according to claim 1, wherein said hollow cage comprises an upper axial wall and a lower axial wall, each axial wall comprising wall portions and axial openings.

9. The device according to claim 8, wherein, in the rest position, an upper axial edge of said first support member is locked axially by a wall portion of said upper axial wall, and a lower axial edge of said second support member is locked axially by a wall portion of said lower axial wall.

10. The device according to claim 9, wherein, when said actuating button is moved radially to its actuating position, an axial opening of said upper axial wall is configured to be positioned facing said upper axial edge of said first support member, and an axial opening of said lower axial wall is configured to be positioned facing said lower axial edge of said second support member.

11. The device according to claim 1, wherein, in the rest position, said flexible tube is deformed and/or twisted, and when said first and second support members move axially relative to one another to their respective actuating positions, said flexible tube is configured to straighten, to compensate for an axial gap generated between the first and second support members during actuation.

12. The device according to claim 1, wherein, during actuation, said fluid product vessel and said compressed gas vessel are configured to be opened simultaneously.

13. The device according to claim 1, wherein, during actuation, said fluid product vessel is configured to be opened just before said compressed gas vessel.

14. The device according to claim 1, wherein said fluid product vessel is a BFS (Blow-Fill Seal) or FFS (Form-Fill Seal), produced by blowing or forming, filling and sealing continuously.

15. The device according to claim 1, wherein said fluid product vessel comprises attachment means for attaching said fluid product vessel to said intermediate portion, removably.

* * * * *